United States Patent [19]

Sumrell et al.

[11] 4,199,460

[45] Apr. 22, 1980

[54] FATTY ACID-DERIVED LUBRICANTS AND ADDITIVES

[75] Inventors: Gene Sumrell; Robert R. Mod, both of New Orleans; Frank C. Magne, Metairie, all of La.; Ronald E. Koos, Lansdale, Pa.

[73] Assignee: The United States of America as represented by the Secretary of Agriculture, Washington, D.C.

[21] Appl. No.: 945,977

[22] Filed: Sep. 26, 1978

[51] Int. Cl.$^2$ ............................................. C10M 1/48
[52] U.S. Cl. ................... 252/46.7; 252/46.6; 252/48.6; 252/54.6; 260/399; 260/408; 544/337
[58] Field of Search ................ 252/46.6, 46.7, 48.6, 252/54.6; 260/399, 408; 544/337

[56] References Cited

U.S. PATENT DOCUMENTS

| | | | |
|---|---|---|---|
| 3,020,305 | 2/1962 | Chupp | 252/46.7 X |
| 3,193,501 | 7/1965 | Matson | 252/46.7 |
| 3,359,203 | 12/1967 | O'Halloran | 252/46.6 |
| 3,536,812 | 10/1970 | Oswald et al. | 252/46.6 X |
| 3,574,795 | 7/1971 | Oswald et al. | 252/46.6 X |
| 3,646,172 | 2/1972 | Myers | 252/46.6 X |
| 3,746,644 | 7/1973 | Magne et al. | 252/47.5 |

OTHER PUBLICATIONS

Mod et al., J.O.A.O.C.S., vol. 54, No. 12, pp. 589–591, 1977 (Dec.).
Perlstein et al., J. Am. Oil Chemists Soc., 51: 335–339, (1974).
Magne et al., J. Am. Oil Chemists Soc., 51: 93–100, (1974).
Magne et al., J. Am. Oil Chemists Soc., 52: 494–497, (1975).
Kenny et al., Lubrication Engineering, pp. 394–397, Aug. 1974.
Parker et al., J. Am. Oil Chemists Soc., 52: 124a, (1975).
Hermann et al., J. Am. Oil Chemists Soc., 51: 88–92, (1974).

*Primary Examiner*—Andrew Metz
*Attorney, Agent, or Firm*—M. Howard Silverstein; David G. McConnell

[57] ABSTRACT

This invention relates to addition products of dialkylphosphorodithioic acid, hexachlorocyclopentadiene, or bromotrichloromethane to unsaturated or epoxy fatty acid amides and esters. These products are useful as extreme pressure lubricants and additives.

22 Claims, No Drawings

FATTY ACID-DERIVED LUBRICANTS AND ADDITIVES

BACKGROUND OF THE INVENTION (1) Field of the Invention

This invention involves novel compositions of matter derived from fatty acid amides and esters which are found to be useful as extreme pressure lubricants and additives.

(2) Description of the Prior Art

The embargo on the importation of sperm whale oil and its products into the United States has spurred intensive search for satisfactory substitutes. Especially required are extreme pressure lubricants and antiwear and extreme pressure additives. An obvious substitute for sperm oil would be a closely similar synthetic composition of esterified fatty alcohols and acids. Such compositions have been shown to be technically feasible, but are of dubious economics because of the involved process required (T. Perlstein et al., J. Am. Oil Chemists' Soc. 51: 335-339 (1974)). Many N-substituted amides of fatty acids or fatty esters containing one or more thiirane groups are good extreme pressure lubricants and effective antiwear and extreme pressure additives for paraffin or diester base lubricants (F. C. Magne, et al., J. Am. Oil Chemists' Soc. 51: 93-100 (1974), and ibid., 52: 494-497 (1975); U.S. Pat. No. 3,746,644). However, satisfactory stabilization of the thiirane ring to prevent polymerization at the high temperatures reached in some lubrication systems has not been solved. Various sulfurized fat- and fatty acid-derived materials have been investigated as replacements for sulfurized sperm oil (H. E. Kenny, et al., Lubrication Engineering, pp. 394-397, August 1974; W. E. Parker, et al., J. Am. Oil Chemists' Soc. 52: 124A (1975); C. L. Hermann and J. J. Glade, J. Am. Oil Chemists' Soc. 51:88-92 (1974). Many of the materials have utility in some of the areas served by sperm oil, but to date no single material has been found which can replace sperm oil or its sulfurized modification in all their varied uses, and the search is continuing for suitable replacements.

SUMMARY OF THE INVENTION

This invention relates to certain compounds which are modified fatty esters and amides, and which have exhibited utility as extreme pressure (EP) lubricants, or lubricant additives. More particularly, this invention relates to long chain aliphatic esters and amides modified by addition to one or more double bonds of 0,0-dialkylphosphorodithioic acid, bromotrichloromethane, or of hexachlorocyclopentadiene. The N-alkyl group or groups of the amides, or the alcohol moiety of the esters may also be similarly modified.

DESCRIPTION OF THE PREFERRED EMBODIMENTS

The compounds which are the subject of this invention are as follows:

3-(0,0-Diethylphosphorodithio)propyl 11-0,0-diethylphosphorodithoundecanoate 0,0-Dibutylphosphorodithioic acid tetrathioester reaction product with N-tris(epoxystearoyloxymethyl)methylepoxystearamide Bis[2-(pentachlorostearoyloxy)ethyl] disulfide 2(3)-(0,0-Diisopropylphosphorodithio)propyl pentachlorostearate 0,0-Dibutylphosphorodithioic acid tetrathioester addition product with N-tris(oleoyloxymethyl)methyloleamide 1,4-Bis[1,2(3)-dicarbobutoxy-3(2)-(9(10)-dibutylphosphorodithiocarbostearoxy)propyl]piperazine 2,2'-Oxybis[ethyl 9(10)-bromo-10(9)-trichloromethylstearate]

2,2'-Thiobis[ethyl 9(10)-bromo-10(9)-trichloromethylstearate]

2,2'-Thiobis[ethyl 8-(1,4,5,6,7,7-hexachloro-3-octylbicyclo-[2.2.1]-5-hepten-2-yl)octanoate]

(2-Ethoxyethoxy)ethyl [-(1,4,5,6,7,7-hexachloro-3-octylbicyclo-[2.2.1]-5-hepten-2-yl)octanoate]

3-(0,0-Diethylphosphorodithio)propyl 9(10)-bromo-10(9)-trichloromethylstearate

These compounds were evaluated as EP lubricants or additives in a Shell 4-ball EP tester at 1440 r.p.m. following ASTM Procedure D2596-67T. Loads were increased in increments of 20 kg. to weld point and the test run for one minute or to weld whichever occurred first. Commercial hypoid fluid SAE #90 was employed as the control EP lubricant. The tester had a load capacity of 600 kg.

Specific examples showing the preparation of each of the new compounds are set forth below along with appropriate data in Table I which establish the performance of these compounds as EP lubricants or additives to a paraffin base oil or a diester base oil. The materials are effective extreme pressure lubricants in the neat condition, or as additives to paraffin or diester base oils at a concentration of 5% or more.

EXAMPLE 1

3-(0,0-Diethylphosphorodithio)propyl 11-0,0-diethylphosphorodithioundecanoate. —10 grams (0.04 mole) of allyl undecenoate and 24.9 grams (0.13 mole) of 0,0-diethylphosphorodithioic acid were placed in a flask, mixed well and exposed to a cobalt-60 (gamma radiation) source to initiate a free radical chain reaction. After irradiating for 24 hours, the mixture was removed from the irradiation source, dissolved in benzene, placed in a flask equipped with stirring bar, neutralized with 5% sodium carbonate, washed with water, dried over anhydrous sodium carbonate, filtered, and stripped. The product had a sulfur content of 19.94%.

EXAMPLE 2

Tetrathioester reaction product of 0,0-dibutylphosphorodithioic acid and N-[tris(9,10-epoxystearoyloxymethyl)methyl]-9,10-epoxystearamide.

A. N-/Tris(oleoyloxymethyl)methyl/oleamide (I).—A sample of 24.2 grams (0.20 mole) of tris(hydroxymethyl)aminomethane was refluxed with 230 grams (0.80 mole) of oleic acid in the presence of benzene until water of condensation was no longer evolved. The crude mixture was washed with aqueous HCl, water, dried over anhydrous Na$_2$SO$_4$, passed through an activated alumina column and stripped.

B. Epoxidation of I.—80 grams of the product of the above reaction was epoxidized by the dropwise addition (with stirring) of a chloroform solution of m-chloroperbenzoic acid containing 47 grams of the peracid. Excess peracid was reduced with a 10% solution of sodium thiosulfite, after which, the total acid was washed out with a 10% solution of NaHCO$_3$. The product was washed with water, dried over anhydrous Na$_2$SO$_4$, filtered and stripped.

C. Preparation of the tetrathioester.—A sample of 64.8 grams (0.28 mole) of O,O-dibutylphosphorodithioic acid was added dropwise with stirring and under a nitrogen blanket to 82.8 grams (0.08 mole) of the epoxidized product. The very viscous mixture was diluted with 50 ml of benzene and 50 ml. of absolute ethyl alcohol and warmed with stirring to 60° C. for two hours. The mixture was dissolved in diethyl ether and washed with a 10% solution of Na$_2$SO$_4$, filtered and stripped. The product had a sulfur content of 11.51%.

EXAMPLE 3

Bis[2-(pentachlorostearoyloxy)ethyl] disulfide.—Samples of 22.5 grams (0.05 mole) of pentachlorostearic acid, 3.9 grams (0.05 mole) of mercaptoethanol, 1 gram of p-toluenesulfonic acid and 50 ml of benzene were mixed and refluxed for 16 hours, the water of reaction being concurrently removed by a Dean-Stark trap. The reaction mixture was transferred to a 250 ml Erlenmeyer flask, 50 ml of water and a stirring bar inserted, and iodine added to the stirred mixture until the iodine color remained. A small amount of sodium bicarbonate was added carefully to neutralize the HI. The organic phase was separated, washed several times with water, dried and stripped. The product had a sulfur content of 7.54%.

EXAMPLE 4

2(3)-(O,O-Diisopropylphosphorodithio)propyl pentachlorostearate.

A. Allyl pentachlorostearate.—130 grams (0.29 mole) of pentachlorostearic acid, 30 grams (0.52 mole) of allyl alcohol and 1 gram of p-toluenesulfonic acid were refluxed in the presence of benzene for 12 hours. The crude product was washed repeatedly with water, once with 10% sodium bicarbonate, followed by several water washings, dried and stripped.

B. 2(3)-(O,O-Diisopropylphosphorodithio)propyl pentachlorostearate.—83.7 grams (0.17 mole) of allyl pentachlorostearate was heated with 40 grams (0.19 mole) of O,O-diisopropylphosphorodithioic acid for 8 hours at 60°-70° C. under a nitrogen blanket. The crude product was dissolved in ether and washed with aqueous sodium carbonate to remove any unreacted acid. After washing with water, the ether layer was dried and stripped. The product had a chlorine content of 31.61%.

EXAMPLE 5

O,O-Dibutylphosphorodithioic acid tetrathioester addition product with N-tris(oleoyloxymethyl)methyloleamide.—To 23.4 grams (0.02 mole) of N-tris-(oleoyloxymethyl)methyloleamide was added a sample of 19.3 grams (0.08 mole) of O,O-dibutylphosphorodithioic acid and the mixture heated at 60°-70° C. for 10 hours. The reaction mixture was then dissolved in ether, washed with 150 ml of 10% sodium carbonate, followed by water washings, dried with anhydrous sodium sulfate, filtered, and stripped. The product had a sulfur content of 8.20%.

EXAMPLE 6

1,4-Bis[1,2(3)-dicarbobutoxy-3(2)-(9(10)-O,O-dibutylphosphorodithiocarbostearoxy)propyl]piperazine.—A sample of 68.4 grams (0.20 mole) of tributyl aconitate was heated with 536 grams (2.0 moles) of oleyl alcohol in the presence of sodium methoxide at 80° C. under full forepump vacuum until there was no further elimination of butyl alcohol. The crude product was washed with aqueous HCl, followed by water, dried, and percolated through an activated alumina column, then stripped. A sample of 77.2 g. of this product was heated at 90° C. with 9.7 grams of anhydrous piperazine with stirring for 15 hours. The reaction mixture was dissolved in a 1:1 solution of benzene and hexane and washed several times with water, dried, and stripped. Samples of 23.2 grams of the resulting product and 9.7 g. of O,O-dibutylphosphorodithioic acid were heated at 60°-70° C. for 8 hours with stirring. The crude reaction product was dissolved in diethyl ether and washed 3 times with 35 ml of 10% sodium carbonate, followed by several water washes, then was dried over anhydrous Na$_2$SO$_4$, filtered and stripped. The product had a sulfur content of 5.92%.

EXAMPLE 7

2,2'-Oxy bis[ethyl 9(10)-bromo-10(9)-trichloromethylstearate].—20 grams (0.03 mole) of 2,2'oxybis(ethyl oleate) and 36 grams (0.18 mole) of bromotrichloromethane were placed in a flask, mixed well, and exposed to a cobalt-60 (gamma radiation) source to initiate a free radical chain reaction. The mixture was removed from the irradiation source after 19 hours, and the excess bromotrichloromethane removed by stripping at reduced pressure. The residue was dissolved in benzene, passed through a column of activated alumina, eluted with a mixture of 1:1 benzeneethanol, and stripped at reduced pressure. The product had a bromine content of 18.33%.

EXAMPLE 8

2,2'-Thiobis[ethyl 9(10)-bromo-10(9)-trichloromethylstearate].—This compound was prepared by the procedure of Example 7 from 15 grams (0.02 mole) of 2,2'-thiobis(ethyl oleate) and 9.1 grams (0.05 moles) of bromothrichloromethane. The product had a bromine content of 15.60%.

EXAMPLE 9

2,2'-Thiobis[ethyl 8-(1,4,5,6,7,7-hexachloro-3-octylbicyclo-[2.2.1]-5-hepten-2-yl)octanoate].

A. Hexachlorocyclopentadiene adduct of oleic acid (II).—Oleic acid (150 grams, 0.53 mole) and hexachlorocyclopentadiene (295 grams, 1.08 moles) were heated under nitrogen in a flask equipped with a condenser for 28 hours at 135° C. The excess hexachlorocyclopentadiene was removed by distillation under reduced pressure, after which, the remaining unadducted oleic acid was removed by complexing with urea in methanol solution and filtering off the solid complex.

B. 2,2'-Thiobis[ethyl 8-(1,4,5,6,7,7-hexachloro-3-octylbicyclo-[2.2.1]-5-hepten-2-yl)octanoate].—II(137 grams, 0.25 mole), 2,2'-thiodiethanol (13.8 grams, 0.11 mole), 50 ml of benzene, and 0.5 grams of 2-naphthalenesulfonic acid were placed in a flask equipped with reflux condenser and Dean-Stark trap. The temperature was raised to reflux and maintained there until water ceased to azeotrope. The reaction mixture was passed through an activated alumina column and stripped of solvent. The product had a sulfur content of 2.20%.

EXAMPLE 10

2-(2-Ethoxyethoxy)ethyl 8-(1,4,5,6,7,7-hexachloro-3-octylbicyclo-[2.2.1]-5-hepten-2-yl)octanoate.—150 grams (0.38 mole) of 2-(2-ethoxyethoxy)ethyl oleate and 205.3 grams (0.75 mole) of hexachlorocyclopentadiene were placed in a flask equipped with a condenser, nitrogen inlet tube, and thermometer. The temperature was raised to 136° C. and maintained there for 30 hours. The excess hexachlorocyclopentadiene was removed by distillation under reduced pressure and the unadducted 2-(2-ethoxyethoxy)ethyl oleate was removed by the urea complex method. The product has a chlorine content of 31.76%.

EXAMPLE 11

3-(0,0-Diethylphosphorodithio)propyl 9(10)-bromo-10(9)-trichloromethylstearate.

A. 3-(0,0-Diethylphosphorodithio)propyl oleate (III).—21 grams (0.07 mole) of allyl oleate and 18.1 grams (0.10 mole) of 0,0-diethylphosphorodithioic acid were placed in a flask, mixed well, and irradiated in a cobalt-60 facility for 22 hours. The mixture was dissolved in benzene, neutralized with 5% sodium carbonate, washed with water, dried over anhydrous sodium sulfate, filtered and stripped.

B. 3-(0,0-Diethylphosphorodithio)propyl 9(10)-bromo-10(9)-trichloromethylstearate.—20 grams (0.04 mole) of III and 15.6 grams (0.08 mole) of bromotrichloromethane were placed in a flask, mixed well, and irradiated in a cobalt-60 facility for 24 hours. The excess bromotrichloromethane was removed by distillation at reduced pressure. The product had a sulfur content of 8.25%.

acid tetrathioester reaction product with N-tris(epoxystearoyloxymethyl)methylepoxystearamide.

3. An extreme pressure lubricant composition comprising a major portion of a paraffin or diester base oil containing in an amount to supply extreme pressure properties the additive bis[2-(pentachlorostearoyloxy)ethyl] disulfide.

4. An extreme pressure lubricant composition comprising a major portion of a paraffin or diester base oil containing in an amount to supply extreme pressure properties the additive 2(3)-(0,0-diisopropylphosphorodithio)propyl pentachlorostearate.

5. An extreme pressure lubricant composition comprising a major portion of a paraffin or diester base oil containing in an amount to supply extreme pressure properties the additive 0,0-dibutylphosphorodithioic acid tetrathioester addition product with N-tris-(oleoyloxymethyl)methyloleamide.

6. An extreme pressure lubricant composition comprising a major portion of a paraffin or diester base oil containing in an amount to supply extreme pressure properties the additive 1,4-bis[1,2(3)-dicarbobutoxy-3(2)-(9(10)-dibutylphosphorodithiocarbostearoxy)-propyl]piperazine.

7. An extreme pressure lubricant composition comprising a major portion of a paraffin or diester base oil containing in an amount to supply extreme pressure properties the additive 2,2'-oxybis[ethyl 9(10)-bromo-10(9)-trichloromethylstearate].

EXTREME PRESSURE LUBRICATING CHARACTERISTICS OF SOME ESTERS AND AMIDES OF SUBSTITUTED FATTY ACIDS

| | | Extreme Pressure Tests | | | | | | |
|---|---|---|---|---|---|---|---|---|
| | | Neat | | | 5% in Base Oil | | | |
| | | | | | Weld pt (kg) | | Scar Dia.[b] (mm) | |
| Sample Number | Compound | Load (kg) | Scar (mm) | Weld pt (kg) | Topaz | DOS | Topaz | DOS |
| 1 | 3-(0,0-Diethylphosphorodithio)propyl 11-0,0-diethylphosphorodithioundecanoate | — | — | 400 | 250 | 200 | 3.90 | 3.00 |
| 2 | 0,0-Dibutylphosphorodithioic acid tetrathioester reaction product with N-tris-(epoxystearoyloxymethyl)methylepoxystearamide | 600 | 3.55 | [a] | 250 | 250 | 3.60 | 3.18 |
| 3 | Bis[2-(pentachlorostearoyloxy)ethyl] disulfide | 400 | 1.33 | 500 | 320 | 280 | 3.18 | 3.05 |
| 4 | 2(3)(0,0-Diisopropylphosphorodithio)propyl pentachlorostearate | 600 | 1.55 | [a] | 200 | 180 | 3.30 | 3.10 |
| 5 | 0,0-Dibutylphosphorodithioic acid tetrathioester addition product with N-tris(oleoyloxymethyl)methyl oleamide | 300 | 1.81 | 400 | 220 | 200 | 3.20 | 3.20 |
| 6 | 1,4-Bis[1,2(3)-dicarbobutoxy-3(2)-(9(10)-dibutylphosphorodithiocarbostearoxy)propyl]piperazine | 250 | 2.25 | 300 | 160 | 180 | 2.16 | 3.80 |
| 7 | 2,2'-Oxybis[ethyl 9(10)-bromo-10(9)-trichloromethylstearate] | 400 | 1.53 | 500 | 240 | 180 | 3.05 | 3.45 |
| 8 | 2,2'-Thiobis[ethyl 9(10)-bromo-10(9)-trichloromethylstearate] | 600 | 1.45 | [a] | 200 | 200 | 3.23 | 2.45 |
| 9 | 2,2'-Thiobis[ethyl 8-(1,4-5,6,7,7-hexachloro-3-octylbicyclo-[2.2.1]-5-hepten-2-yl)octanoate] | 600 | 1.43 | [a] | 180 | 200 | 2.08 | 2.59 |
| 10 | (2-Ethoxyethoxy)ethyl [8-(1,4,5,6,7,7-hexachloro-3-octylbicyclo[2.2.1]-5-hepten-2-yl)octanoate] | 600 | 1.41 | [a] | 180 | 180 | 2.70 | 3.15 |
| 11 | 3-(0,0-Diethylphosphorodithio)propyl 9(10)-bromo-10(9)-trichloromethylstearate | 600 | 1.20 | [a] | 280 | 220 | 2.70 | 2.72 |
| Control Topaz 105 sec oil | | — | — | 120 | — | — | — | — |
| Control Di 2-ethylhexyl sebacate (DOS) | | — | — | 110 | — | — | — | — |
| Control SAE #90 Comm. hypoid fluid | | — | 2.60 | 280 | — | — | — | — |

[a]Beyond capacity of 4-ball tester
[b]Scar diameter at highest non-weld load

We claim:

1. An extreme pressure lubricant composition comprising a major portion of a paraffin or diester base oil containing in an amount to supply extreme pressure properties the additive 3-(0,0-diethylphosphorodithio)propyl 11-0,0-diethylphosphorodithioundecanoate.

2. An extreme pressure lubricant composition comprising a major portion of a paraffin or diester base oil containing in an amount to supply extreme pressure properties the additive 0,0-dibutylphosphorodithioic 8. An extreme pressure lubricant composition comprising a major portion of a paraffin or diester base oil containing in an amount to supply extreme pressure properties the additive 2,2'-thiobis[ethyl 9(10)-bromo-10(9)-trichloromethylstearate].

9. An extreme pressure lubricant composition comprising a major portion of a paraffin or diester base oil containing in an amount to supply extreme pressure properties the additive 2,2'-thiobis[ethyl 8-(1,4,5,6,7,7- hexachloro-3-octylbicyclo[2.2.1]-5-hepten-2-yl)octanoate].

10. An extreme pressure lubricant composition comprising a major portion of a paraffin or diester base oil containing in an amount to supply extreme pressure properties the additive (2-ethoxyethoxy)ethyl [8-(1,4,5,6,7,7-hexachloro-3-octylbicyclo[2.2.1]-5-hepten-2-yl)octanoate].

11. An extreme pressure lubricant composition comprising a major portion of a paraffin or diester base oil containing in an amount to supply extreme pressure properties the additive 3-(0,0-diethylphosphorodithio)-propyl 9(10)-bromo-10(9)-trichloromethylstearate.

12. The compound 3-(0,0-diethylphosphorodithio)-propyl 11-0,0-diethylphosphorodithioundecanoate.

13. The compound 0,0-dibutylphosphorodithioic acid tetrathioester reaction product with N-tris(epoxystearoyloxymethyl)methylepoxystearamide.

14. The compound bis[2-(pentachlorostearoyloxy)ethyl]disulfide.

15. The compound 2(3)-(0,0-diisopropylphosphorodithio)propyl pentachlorostearate.

16. The compound 0,0-dibutylphosphorodithioic acid tetrathioester addition product with N-tris(oleoyloxymethyl)methyloleamide.

17. The compound 1,4-bis[1,2(3)-dicarbobutoxy-3(2)-(9(10)-dibutylphosphorodithio-carbostearoxy)propyl]-piperazine.

18. The compound 2,2'-oxybis[ethyl 9(10)-bromo-10(9)-trichloromethylstearate].

19. The compound 2,2'-thiobis[ethyl 9(10)-bromo-10(9)-trichloromethylstearate].

20. The compound 2,2'-thiobis[ethyl 8-(1,4,5,6,7,7-hexachloro-3-octylbicyclo-[2.2.1]-5-hepten-2-yl)octanoate].

21. The compound (2-ethoxyethoxy)ethyl [8-(1,4,5,6,7,7-hexachloro-3-octylbicyclo-[2.2.1]-5-hepten-2-yl)octanoate].

22. The compound 3-(0,0-diethylphosphorodithio)-propyl 9(10)-bromo-10(9)-trichloromethylstearate.

* * * * *